(12) United States Patent
Van Ooijen et al.

(10) Patent No.: US 11,567,089 B2
(45) Date of Patent: Jan. 31, 2023

(54) METHOD FOR DETERMINING THE FIBRINOGEN CONCENTRATION IN A BIOLOGICAL SAMPLE

(71) Applicant: KONINKLIJKE PHILIPS N.V., Eindhoven (NL)

(72) Inventors: Hendrik Jan Van Ooijen, Wijk en Aalburg (NL); Bart Jacob Bakker, Eindhoven (NL); Rene Van Den Ham, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 776 days.

(21) Appl. No.: 15/536,307

(22) PCT Filed: Dec. 18, 2015

(86) PCT No.: PCT/EP2015/080535
§ 371 (c)(1),
(2) Date: Jun. 15, 2017

(87) PCT Pub. No.: WO2016/097312
PCT Pub. Date: Jun. 23, 2016

(65) Prior Publication Data
US 2017/0363650 A1 Dec. 21, 2017

(30) Foreign Application Priority Data
Dec. 18, 2014 (EP) ..................................... 14198872

(51) Int. Cl.
*G01N 33/86* (2006.01)
(52) U.S. Cl.
CPC ......... *G01N 33/86* (2013.01); *G01N 2333/75* (2013.01)
(58) Field of Classification Search
None
See application file for complete search history.

(56) References Cited

U.S. PATENT DOCUMENTS

| 4,461,830 A | 7/1984 | Philpot |
| 5,118,182 A | 6/1992 | Carr |
| 5,156,974 A | 10/1992 | Grossman et al. |
| 5,223,437 A | 6/1993 | Hoffman et al. |
| 5,670,329 A | 9/1997 | Oberhardt |
| 8,936,753 B2 | 1/2015 | Yamamoto et al. |
| 2014/0356880 A1 | 12/2014 | Hanko |

FOREIGN PATENT DOCUMENTS

EP 0059277 A1 9/1982

OTHER PUBLICATIONS

Van Der Bom, J.G. et a., "Elevated Plasma Fibrinogen. Cause or Consequence of Cardiovascular Disease?" Arterioscler, Thromb. Vase. Biol. (1998) 18(4):621-625.
Rooney, T. et al., "Levels of plasma fibrinogen are elevated in well-controlled rheumatoid arthritis", Rheumatology (2011) 50(8):1458-1465.
Palareti, G. et al., "Fibrinogen assays: a collaborative study of six different methods. C.I.S.M.E.L. Comitato Italiano per la Standardizzazione dei Metodi in Ematologia e Laboratorio", Clinical Chemistry (1991) 37(5):714-719.
Carr, M.E. et al., "Dextran-Induced Changes in Fibrin Fiber Size and Density Based on Wavelength Dependence of Gel Turbidity", Macromolecules (1980) 13(6): 1473-1477.
Ellison, S. et al: "Standard additions: myth and reality", The Analyst, vol. 133, No. 8, Jan. 1, 2008, p. 992.
Chen, W., "A non-clotting and non-instrumental method for sensing heparin and monitoring of extracorporeal anticoagulation", ProQuest Dissertations & Theses Full Text: The Sciences and Engineering Collection, Jan. 1, 1991, pp. 1-147.
Kamath, S. et al., "Fibrinogen: biochemistry, epidemiology and determinants" QJ Med. (2003) 96(10):711-729.

*Primary Examiner* — G Steven Vanni

(57) ABSTRACT

The present invention relates to clinical decision support systems. In detail, the present invention relates to a method for determining the initial fibrinogen concentration in a biological sample, to the use of fibrinogen added to a biological sample in at least one predetermined concentration, to a device for determining the initial fibrinogen concentration in a biological sample, to a computer program comprising program code means for causing a computer to carry out at least several steps of the method according to the invention, to a computer readable non-transitory storage medium containing instructions for carrying out at least some steps of the method according to the invention, and to a kit for determining the initial fibrinogen concentration in a biological sample.

9 Claims, 3 Drawing Sheets

METHOD FOR DETERMINING THE FIBRINOGEN CONCENTRATION IN A BIOLOGICAL SAMPLE

CROSS-REFERENCE TO PRIOR APPLICATIONS

This application is the U.S. National Phase application under 35 U.S.C. § 371 of International Application No. PCT/EP2015/080535, filed on Dec. 18, 2015, which claims the benefit of European Patent Application No. 14198872.5, filed on Dec. 18, 2014. These applications are hereby incorporated by reference herein.

FIELD OF THE INVENTION

The present invention relates to clinical decision support systems. In detail, the present invention relates to a method for determining the initial fibrinogen concentration in a biological sample, to the use of fibrinogen added to a biological sample in at least one predetermined concentration, to a device for determining the initial fibrinogen concentration in a biological sample, to a computer program comprising program code means for causing a computer to carry out at least several steps of the method according to the invention, to a computer readable non-transitory storage medium containing instructions for carrying out at least some steps of the method according to the invention, and to a kit for determining the initial fibrinogen concentration in a biological sample.

BACKGROUND OF THE INVENTION

Fibrinogen is an important protein involved in coagulation. During normal blood flow, fibrinogen is soluble; however upon activation of the coagulation system fibrinogen is eventually converted by thrombin into fibrin. Fibrin subsequently polymerizes into insoluble fibrin fibers that, together with preferably activated platelets, form a clot. The normal concentration of fibrinogen is approximately 2.5 g/l with a range of about 1.5 to 3 g/l [Greer et al. (Ed.), Wintrobe's Clinical Hematology, 11$^{th}$ edition, page 720]. Yet in many cases the fibrinogen concentration can be outside the normal range, which might be associated with pathological disorders. For example, in hereditary hypofibrinogenemia patients the low concentration of fibrinogen due to sustained bleeding results in a dangerous situation which can be countered by the addition of blood products. On the other side of the spectrum elevated concentrations of fibrinogen are found to be correlated with an elevated risk of myocardial infarction (Bom et al., Arterioscler. Thromb. Vasc. Biol. (1998) 18(4): 621-625), thrombosis (Kamath and Lip, Q. J. Med. (2003) 96(10): 711-729) and prolonged inflammatory processes such as rheumatoid arthritis (Rooney et al., Rheumatology (2011) 50(8): 1458-1465). As a result of these varying fibrinogen concentrations and associated pathologies, the fibrinogen concentration test is a valuable clinical test. Unfortunately however, reliable point of care (POC) fibrinogen tests are not available and central lab test ordering in general takes to long for time critical situations, for example in the operating theater.

Numerous methods have been developed intending to accurately detect the level of fibrinogen in a plasma or blood sample (see for example Palarati et al., Clinical Chemistry (1991) 37(5): 714-719, for an overview of available techniques or EP 2 259 069).

Unfortunately all presently available methods are either very labor-intensive, such as the clot-recovery method, or need a calibration curve derived from a plasma sample with a known fibrinogen level to infer the sample's fibrinogen level, such as the Clauss assay or prothrombin-time-derived method. Whereas the former involves a lot of hands on time and therefore is difficult to automate, the latter needs calibration plasmas to be included in the test protocol. Such a method requiring at least two reference samples of blood plasma to calibrate the measurement is disclosed in EP 0 059 277. These kinds of methods are, however, not suitable for being incorporated in an automated device, e.g. a hand held point of care (POC), to detect the level of fibrinogen.

SUMMARY OF THE INVENTION

It is an object of the invention to provide a method for determining the initial fibrinogen concentration in a biological sample by means of which the disadvantages of the prior art methods can be avoided. In particular, such a method for determining the initial fibrinogen concentration in a biological sample should be provided which allows a reliable determination on whether a subject the biological sample originates from has a bleeding tendency or the risk of developing thrombosis or other pathologies associated with the fibrinogen level in the subjects' or patients' body fluids, such as blood or blood plasma, respectively.

It is another object of the invention to provide a device for determining the initial fibrinogen concentration in a biological sample, a computer program comprising program code means for causing a computer to carry out at least some of the steps of the method according to the invention, a computer readable none transitory storage medium containing said computer program, and a kit for determining the initial fibrinogen concentration in a biological sample.

In a first aspect of the present invention a method for determining the initial fibrinogen concentration in a biological sample is presented, said method comprises the following steps:
(1) providing a biological sample;
(2) adding fibrinogen to said biological sample in at least one predetermined concentration;
(3) starting a clotting process in said biological sample;
(4) determining the attenuance of the biological sample as a function of time to obtain an attenuance curve;
(5) extracting feature values indicative of the fibrinogen concentration in said biological sample from said attenuance curve and recording them as a function of fibrinogen added in step (2);
(6) calculating a fitted function through said recorded feature values of step (5);
(7) determining the initial fibrinogen concentration in said biological sample from said fitted function of step (6).

In another aspect of the present invention the use of fibrinogen added to a biological sample in at least one predetermined concentration for determining the initial fibrinogen concentration in said biological sample is presented.

In still another aspect of the present invention a device is presented for determining the initial fibrinogen concentration in a biological sample, said device is comprising:
(1) a container capable of receiving a biological sample and an addition of fibrinogen in at least one predetermined concentration;

(2) a measuring unit configured for measuring the attenuance of said biological sample;
(3) a calculating unit configured:
  determining the attenuance of the biological sample as a function of time to obtain an attenuance curve;
  extracting feature values indicative of the fibrinogen concentration in said biological sample from said attenuance curve and recording them as a function of fibrinogen to said biological sample;
  calculating a fitted function through said recorded feature values;
  determining the initial fibrinogen concentration in said biological sample from said fitted function.

In still another aspect of the present invention a computer program is presented, said computer program is comprising program code means for causing a computer to carry out at least steps (4), (5), (6), (7) of the method according to the invention.

In still another aspect of the present invention a computer readable non-transitory storage medium is presented, said computer readable non-transitory storage medium is containing instructions for execution by a processor, wherein the instructions caused a processor to carry out at least the steps (4), (5), (6), (7) of the method of the according invention.

In still another aspect of the present invention a kit for determining the initial fibrinogen concentration in a biological sample is presented, said kit is comprising the device according to the invention, fibrinogen, preferably in dry or lyophilized form, further preferably comprising a predetermined amount thereof, a manual for performing the method according to the invention, and optionally a clotting trigger, and further optionally the computer readable non-transitory storage medium according to the invention.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed use, device, computer program, computer readable non-transitory storage medium, and kit have similar and/or identical preferred embodiments as the claimed method and as defined in the dependent claims. Therefore, all of the dependent claims referring to the method according to the invention can also be combined with the use, device, computer program, computer readable non-transitory storage medium and kit according to the invention and with each other.

The inventors herewith present a method that adds at least one, but preferable multiple amount(s) of fibrinogen to the biological sample itself, possibly in parallel experiments, for example divided over a cartridge with multiple detection chambers in a POC device, instead of using a calibration curve constructed from a number of plasmas with known fibrinogen levels or a dilution series of a plasma with known fibrinogen levels. This will result in an internal calibration curve that is within the sample itself, as opposed to an external calibration curve derived from a plasma sample with a known fibrinogen level. The method according to the invention can be automated to be used on e.g. a POC platform with multiple chambers with a known fibrinogen content or concentration, and also does not need calibration plasma to determine a fibrinogen level in the sample. The method according to the invention can also be implemented on central lab devices, which results in the omission or a decrease in the usage of calibration plasma. In addition, internal calibration has the advantage that it will correct for physical properties of the initial sample, such as matrix composition, more appropriately compared to an external calibration.

Using an internal calibration curve by the addition of one or more fibrinogen concentrations to a biological sample to determine its initial concentration of fibrinogen is not known in nor rendered obvious by the prior art.

According to the invention "biological sample" refers to any samples suspected of containing fibrinogen. The biological sample could be of natural or non-natural origin. Preferred are samples of body fluids, in particular such being capable of undergoing blood clotting or coagulation, such as blood samples, blood plasma samples, whole blood samples etc.

According to the invention the "initial fibrinogen concentration" refers to the fibrinogen concentration being present in the biological sample that is provided in step (1), i.e. before any fibrinogen is added in step (2).

According to the invention a "predetermined concentration" refers to the fact that the user has positive knowledge of the added fibrinogen concentration. "Adding fibrinogen" refers to the addition of fibrinogen to the biological sample. "Adding" may also refer to the addition of the biological sample to a predetermined concentration of fibrinogen laid in a container, e.g. in form of a solution of fibrinogen or in dry or lyophilized form.

According to the invention "clotting process" refers to a process that involves the conversion of fibrinogen into fibrin. This conversion is preferably followed by subsequent steps such as the polymerization of fibrin into insoluble fibrin fibers that, together with preferably activated platelets, form a clot. The full clotting process in a blood or blood plasma sample is also referred to as blood coagulation process. The clotting process can e.g. be started by adding so called clotting triggers to the biological sample.

According to the invention "attenuance" refers to a measure of the absorbance of a substance, such as the biological sample, plus losses, e.g. due to scattering and luminescence. The attenuance of a biological sample, such as a coagulating plasma or blood sample, changes over time as a result of the fibrin network being formed during clotting of the sample. Fibrin fibers are being formed after a clotting trigger is added to the sample. These fibrin fibers result in scattering of the incident light resulting in less photons arriving at the detector. Actual absorbance of the photons and other causes of attenuation such as luminescence are considered to be constant over time during clotting, hence the attenuance and thereby decrease in transmittance and increase in optical density is considered solely due to scattering of the incident light by the fibrin fibers formed in the sample. The attenuance of a material is $\log 10(P_0/P)$, where $P_0$ is the radiant power incident on a sample, and P is that transmitted by it. This quantity is also $-\log 10(T)$, where T is the transmittance. Attenuance is often directly related or referred to in the literature by terms such as 'optical density', 'turbidity' or 'extinction'. Also the name 'absorbance' (symbol: A) is often mistakenly used for this quantity, but this is inappropriate for the quantity when the attenuation of the radiation is due to scattering rather than absorption. The quantity itself is called attenuance (symbol: D), with the remark that attenuance reduces to absorbance when there is negligible scattering or reflection. The inventors recognized that in the case that attenuance reduces to scattering, scientist may use the term 'turbidity', which is typically considered as −ln(T). In the latter case, 'turbidity' may be estimated by measuring transmittance. To actually measure scattering due to particles in solution, specialized techniques are available such as small-angle scattering or nephelometry. The attenuance can be converted into the 'turbidity', 'transmittance', 'optical density', 'absorbance' and other measures of light attenuation or scattering due to particles in solution. Therefore, according to the invention the afore-said dimensions or terms can be used instead of the attenuance.

To establish the "attenuance curve" the attenuance values of the biological sample are determined at least for one but preferably for a plurality of points in time in relation to a specific reference point, e.g. the starting point of the clotting process. The attenuance values are then plotted over the time. A typical attenuance curve of a plasma sample is characterized by its "S" shape or sigmoid curve progression, respectively. Alternatively, the attenuance is only measured at the two time points, that is at the starting point of the clotting process and at the end stage of clotting after the clotting process is (nearly) fully developed.

According to the invention "feature values" refer to such information extractable from the attendance curve indicative of the fibrinogen concentration in said biological sample, e.g. by using common mathematical methods such as differential calculus, derivation, integration etc.

When such feature values are recorded as a function of fibrinogen added, according to the invention a "fitted function" can be calculated through said recorded feature values. Such procedure is referred to as "curve fitting" which is the process of constructing a curve or mathematical function that has the best fit to a series of data points. Curve fitting can involve either interpolation, where an exact fit to the data is required, or smoothing, in which a "smooth" function is constructed that approximately fits the data. Curve fitting includes a regression analysis which focusses on questions of statistical inference such as how much uncertainty is present in a curve that is fit to data observed with random errors.

According to the invention the "determination" of the initial fibrinogen concentration in the biological sample from the fitted function is realized by using methods well known in the art, such as extrapolation, including linear, polynomial, conic or French curve extrapolation. For a linear fit the following equation may apply: $fy=\alpha^* fg_{add}+\beta$, with fy as the feature value, $fg_{add}$ the added fibrinogen, and $\alpha$ and $\beta$ the fitting parameters, respectively slope and offset of the linear fit. The fibrinogen concentration may then be $fg_{sample}=-\beta/\alpha$.

In the device according to the invention a "container" refers to any reservoir suited for receiving the biological sample and the fibrinogen, such as a well, cuvette, cartridge, tube etc., possibly divided into a plurality of subreservoirs.

A "measuring unit" includes any measuring tool suited for measuring the attenuance of said biological sample, such as a photometer.

A "calculating unit" refers to a device including hardware and software components, e.g. a processor, computer, processing information such as programs for computer, algorithms etc.

As an alternative to the attenuance curve in all embodiments of the present invention a "mass/length curve" can be used. Mass/length is the average mass of the average fibrin fibers divided by its length. The mass/length curve and the attenuance/optical density/turbidity curve are related to each other by means of an equation extracted from physical properties of fibrin fibers. Here the relation between turbidity and average mass/length ratio is shown exemplarily:

$$\tau = \frac{c}{\lambda^3 \left( \frac{A}{\mu} + \frac{B}{\pi \rho N_A \lambda^2} \right)}$$

with $\tau$ the turbidity as the minus natural logarithm of the transmittance T, $N_A$ being Avogadro's number to transform the density to Da/cm$^3$, $\mu$ being the average mass/length ratio of the fibers in Dalton per centimeter, and A and B being lumped parameters that can be determined in separate experiments or by measuring the optical density of a fixed mass/length ratio of known solute concentrations at different wave lengths. In a preferred embodiment values for A and B at a wavelength of 632.8 nm may be $6.76 \chi 10^{22}$ and $1.41 \chi 10^{24}$, respectively. The relation between attenuance and/or optical density and mass/length ratio follows straightforwardly from this equation.

In this alternative approach the feature values indicative of the fibrinogen concentration in said biological sample are likewise extracted from the mass/length curve. For example the maximum rates observed in the sample with added fibrinogen indicate a linear relationship between the added fibrinogen and maximum rate. This relation can similarly be used to infer the initial fibrinogen concentration of the sample. Feature values extracted from the average mass/length ratio pertaining to the dynamics of the curve can be approximated best by a reciprocal function or alternatively by a power or exponential function.

According to a further development of the method according to the invention said step (7) is realized by the following steps:
(7.1) Extrapolating said fitted function of step (6) to the value of added fibrinogen where said feature value is zero to obtain an extrapolated value;
and/or
Extrapolating said fitted function of step (6) to the value of added fibrinogen to a value that coincides with a hypothetical sample with a fibrinogen level of zero to obtain an extrapolated value;
(7.2) Determining the initial fibrinogen concentration in said biological sample by multiplying said extrapolated value by −1.

According to the invention the "value" of added fibrinogen may refer to any measure reflecting the added fibrinogen, such as the concentration of fibrinogen, e.g. indicated in g/L, or the amount of added fibrinogen, etc.

According to the invention a "hypothetical sample" refers to a sample that is not actually present but a "theoretical sample" as the result of a mathematical operation.

Such embodiments provide reliable results in case a linear fitting has been calculated. An extrapolation of the linear fit to the intersection with the horizontal axis, which corresponds with the feature value in case no fibrinogen would be present in the sample, this value at the intersection indicates the concentration of fibrinogen one needs to add to obtain a zero concentration of fibrinogen in the sample. Hence, this intersection will be at a negative value (or zero) and thus has to be multiplied by −1 to obtain the fibrinogen concentration or level in the initial sample.

Accordingly, in a further development the computer program of the invention is comprising program code means for causing a computer to carry out at least steps (4), (5), (6), (7), (7.1) and (7.2) of the method according to the invention when said computer program is carried out on the computer.

Accordingly, in a further development the computer readable non-transitory storage medium contains instructions for execution by a processor, wherein the instructions cause the processor to carry out at least steps (4), (5), (6), (7), (7.1) and (7.2) of the method according to the invention.

According to a further development of the method of the invention, said feature values indicative of the fibrinogen concentration in said biological sample are selected from:
- difference in attenuance of said biological sample between a first point in time and a second point in time (Δ attenuance), preferably at the starting point of the clotting process as the first point in time, and at the end of the clotting process as the second point in time (Δ attenuance);
- maximum attenuance rate (time derivative of attenuance curve);
- features which correspond with time, including: lag time, time to (a certain degree of) maximum attenuance.

According to the invention "lag time" refers to the point in time at which the attenuance starts to rise quickly due to the formation of fibrin fibers thick enough to significantly scatter the incident photons. Lag time can be found for example by finding the intersection of a tangent at the point of maximum rate and the horizontal line of the attenuance at the starting point of the clotting process or finding the time point of the maximum of the second derivative of the attenuance curve to time or the intersection with an attenuance value, for example 0.1.

All such feature values have been proven being indicative of the fibrinogen concentration in said biological sample. Δ attenuance is a preferred feature extracted from the attenuance curve exemplarily used to demonstrate the enablement of the invention. In case of employing Δ attenuance as the feature value the attenuance will be measured at at least two time points, e.g. at the beginning and after the clotting process has been completed, i.e. as the clotting is (nearly) fully developed. The time span between the two time points may vary, e.g. in dependence of the trigger for starting the clotting process. A preferable time span may be 1-1000 seconds, further preferably 10-500 seconds, and highly preferably 100-200 seconds, in particular in case 1 NIH trombine U/mL is used as the clotting trigger.

According to another aspect said fitted function of step (6) is selected from
- a linear function;
- a non-linear function, including: exponential function, power function, reciprocal function.

Any of such functions may be preferred in fitting the extracted feature values depending on the nature and behavior of the respective feature. As the inventors were able to realize the Δ attenuance plotted against the fibrinogen can be fitted with a linear function. It was also realized by the inventors that features that correspond with time can be fitted with a non-linear function. The latter features go to infinity as the true concentration of fibrinogen in the sample goes to 0. The horizontal (x–) coordinate of the (vertical) asymptote of the fitted curve relates to the negative value of the fibrinogen level in the sample. In case a reciprocal function of the form $\alpha/(fg_{add}-\beta)$ is fitted, which is preferred in case of the features related to points in time, with $fg_{add}$ the concentration of added fibrinogen and $\alpha$, $\beta$ unknown parameters that are fitted with an algorithm, $-\beta$ equals the fibrinogen level of the sample as the vertical asymptote is found at $\beta$. Another feature, the maximum rate of the attenuance curve, is preferably fitted with a function of the form of $\alpha*(fg_{add}-\beta)^2$, with $fg_{add}$ the concentration of added fibrinogen and $\alpha$, $\beta$ unknown, respectively negative and positive, parameters that are fitted with an algorithm. In that case the minimum of the quadratic function can be found at $\beta$, hence $-\beta$ equals the fibrinogen level of the sample as well.

According to another aspect in step (2) said clotting process is started by adding a clotting trigger to said biological sample, preferably selected from the group consisting of:
- active coagulation factors, including: thrombin (F2a), tissue factor (TF), active FX (FXa), active proconvertin (FVIIa);
- snake venom thrombin-like enzymes, including: batroxobin and reptilase;
- kaolinite, micronize silica, ellagic acid.

Said measure has the advantage that the clotting process is effectively started, preferably by providing such clotting triggers which have been proven as being particularly suited for the invention. Though the clotting triggers thrombin (F2a) and snake venom thrombin-like-enzymes are preferred all of the recited clotting triggers are proper initiators of the clotting process and thus provide reliable results.

Preferably the clotting trigger is added to said biological sample in a concentration sufficiently high that the shape of the attenuance curve is essentially determined by the fibrinogen concentration in the biological sample. The amount of fibrinogen in a sample has a high influence on the shape of the attenuance curve and the clotting assay of step (3) can be developed in such a way that at sufficiently high concentrations of thrombin or another clotting trigger with similar activity differences between the attenuance curves of biological samples are (essentially or only) due to their difference in the fibrinogen concentration. Thrombin concentrations above or equal to 1 NIH U/mL are reasonable, higher values of the thrombin concentration are more preferred since this will shorten the assay time and will lower the effect of possible feedback in the system. For the snake venom thrombin-line-enzymes concentrations of 1 or higher BU/mL are reasonable, for the coagulation factors concentrations above 10 nM are preferred.

In another aspect of the method according to the invention in step (1) said biological sample is provided in at least two aliquots allowing the execution of steps (2) to (4) in said at least two aliquots, preferably in parallel, resulting in the obtainment of at least two attenuance curves.

Even though the addition of a plurality of predetermined fibrinogen concentrations may be added to a single aliquot of the biological sample splitting it up to several aliquots to each of which a different predetermined fibrinogen concentration is added can result in more reliable results. "At least two aliquots" and "at least two attenuance curves" include 3, 4, 5, 6, 7, 8, 9, 10, 20, 30, 40, 50, 100, and 1000 etc. aliquots and attenuance curves, respectively, or even more. In a preferred embodiment the biological sample may be provided in a plate or cartridge, comprising multiple wells or chambers. Each of the wells or chambers may contain a known fibrinogen content.

In compliance with this, in another aspect of the device according to the invention said container is a multi-well container capable for receiving at least two aliquots of said biological sample preferably a microtiter plate.

Such multi-well containers or microtiter plates allow the application of the method according to the invention in a large or industrial scale.

In still another aspect of the device of the present invention said measuring unit is an optical measuring system comprising at least one light source and at least one light detector.

This measure has the advantage that such a measuring unit is provided which is particularly suited for working the invention. It goes without saying that the optical measuring system may have 2, 3, 4, 5, and more light sources and detectors, e.g. depending on the number of aliquots of the biological sample and the specific technical requirements of the device.

As recited further above another subject of the invention is the use of fibrinogen added to a biological sample in at least one predetermined concentration for determining the initial fibrinogen concentration in said biological sample.

The inventors have realized that for determining the initial concentration of fibrinogen in a biological sample no external calibration curve constructed from a number of plasmas with known fibrinogen levels is needed. Instead, an internal calibration curve may be used as this has been realized with the invention. Such use can be easily automated, e.g. in form of a POC platform with multiple chambers with a known fibrinogen content and thus no longer the usage of calibration plasma is needed.

It shall be understood that a preferred embodiment of the invention can also be any combination of the dependent claims with the respective independent claims.

These and other aspects of the invention will be apparent from and elucidated with reference to the embodiments described hereinafter.

DETAILED DESCRIPTION OF THE INVENTION

The clotting of the plasma can be initiated by for example tissue factor, kaolin, thrombin or another clotting agent or trigger, respectively. During this clotting, the opacity of a plasma sample changes. This will result in a decrease in light transmission which can be measured by means of the attenuance, optical density or the turbidity of the sample over time (Carr and Gabriel, Macromolecules (1980) 13(6): 1473-1477). The amount of fibrinogen in a sample has a high influence on the shape of the attenuance, optical density or turbidity curve, and the clotting assay can be developed in such a way that at sufficiently high concentration of thrombin or another enzyme with a similar activity towards fibrinogen differences between the attenuance or optical density curves of plasma samples are mainly due to their difference in the fibrinogen concentration. Features extracted from an attenuance curve are therefore indicative of the fibrinogen level in the sample and can be used to construct a calibration curve using addition of known fibrinogen levels to the sample.

In the method according to the invention, the calibration curve based on an external control plasma with a known fibrinogen concentration is replaced by a calibration in the sample of interest itself by the addition of at least one, but preferably several, known fibrinogen concentration(s), preferably to the initial sample. The features of interest from the attenuance curve are extracted from the multiple measurements.

Figure 1:
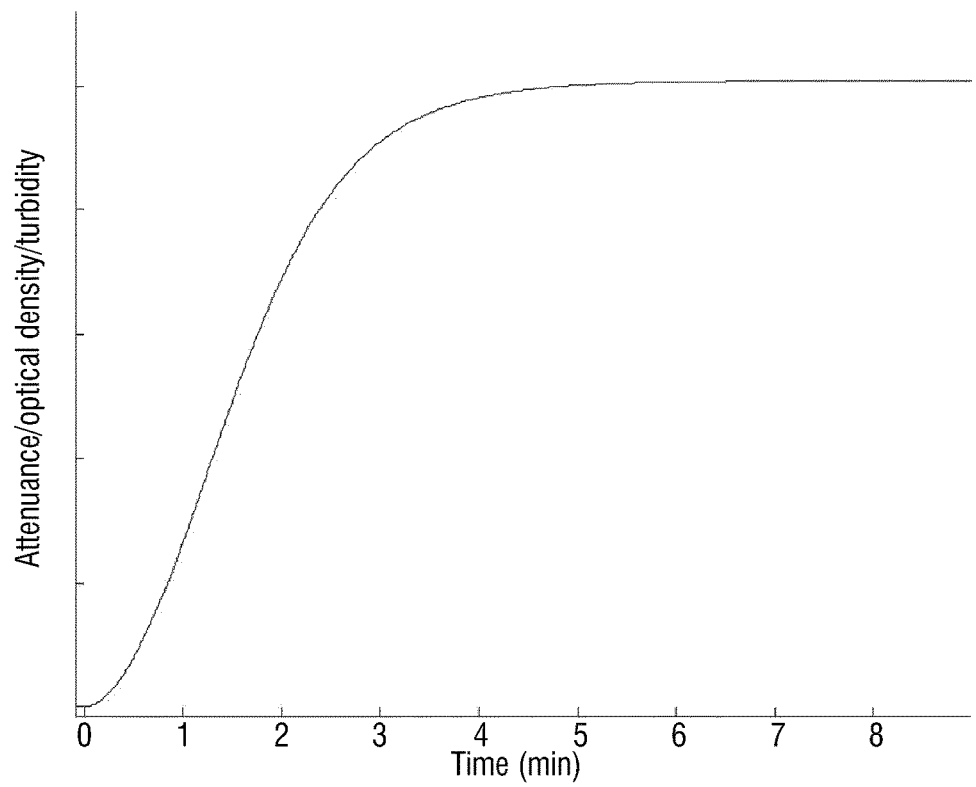
FIG. 1 shows a typical example of attenuance or optical density or turbidity change (on the vertical axis) measured over time (horizontal axis) in a clotting plasma sample initiated by thrombin. After a short lag time in which fibrinogen is converted to fibrin, activated fibrin monomers start to polymerize and form thick fibrin fibers that cause light to scatter which is detectable by a decrease in transmitted light or increase of turbidity or attenuance.
Figure 2:
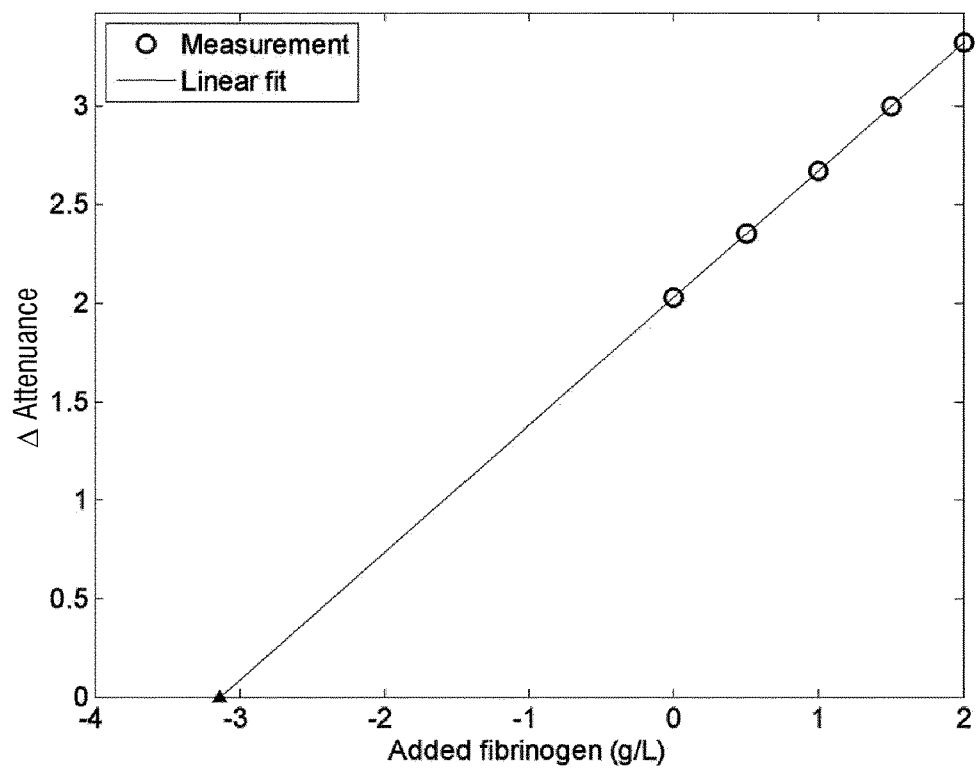
FIG. 2 shows the Δ attenuance in the sample and in sample with the addition of 0.5, 1, 1.5, 2 g/L of fibrinogen (open circles). A linear function can be used to fit the measurement points. An extrapolation of the linear fit to the intersection with the horizontal axis, which corresponds with the Δ attenuance in case no fibrinogen would be present in the sample, indicates that the sample's initial fibrinogen concentration is 3.14159 g/L.

FIG. 2 shows the theoretical difference in attenuance of the sample (as calculated in a model) between the start and end of the measurement, further referred to as Δ attenuance, as a function of the concentration of added fibrinogen (here in grams fibrinogen added per liter plasma sample). The Δ attenuance is a preferred feature from the attenuance curve exemplarily used in this invention. It can be seen in FIG. 2 that this feature varies linearly with added fibrinogen. If no fibrinogen would be present in the sample before adding any fibrinogen, there would be no attenuance change at zero added fibrinogen because no fibrin could be formed. The non-zero value of Δ attenuance of the original sample, i.e. at zero added fibrinogen, indicates the initial concentration of fibrinogen in the sample, i.e. the value that is to be determined by the method according to the invention.

The measurement of a clotting feature, e.g. Δ attenuance, at zero and one or more non-zero values for added fibrinogen is therefore followed by a step that involves the calculation of a fit, sometimes referred to as regression, through the multiple observed feature values. Extrapolation of the fitted curve then yields the original fibrinogen concentration in the plasma sample. For the Δ attenuance feature this works as follows:

estimate a linear fit (Δ attenuance=$\alpha$*$fg_{add}$+$\beta$, with $fg_{add}$ the added fibrinogen and $\alpha$ and $\beta$ fitting parameters, respectively slope and offset of the linear fit);

extrapolate the fitted function to the value of added fibrinogen where the Δ attenuance is zero. This will be a negative value (or zero);

the fibrinogen level in the sample is calculated as minus the extrapolated value. For the linear relationship with added fibrinogen that is followed by Δ attenuance this equals the offset of the line divided by the slope ($fg_{sample}=-\beta/\alpha$).

Figure 3:
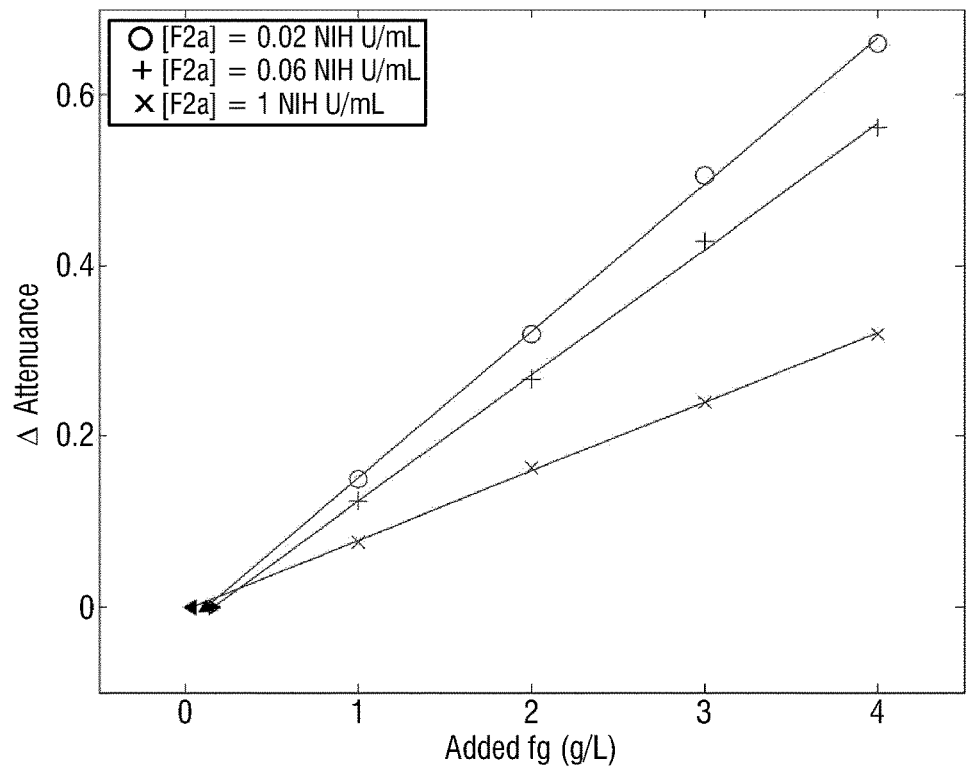
FIG. 3 shows the Δ attenuance observed in fibrinogen deficient plasma added with 1, 2, 3 and 4 g/L of fibrinogen and triggered with 0.02 (o), 0.06 (+) and 1 (x) NIH U/mL. The fitted parameters of the linear function were used to calculate the fibrinogen concentration in the sample using the herein described method and resulted in 0.12 (95%—confidence interval: −0.013-0.24), 0.16 (95%—CI: 0.006-0.29) and 0.033 (95%—CI: —0.074-0.13) g/L fibrinogen, respectively.

The above method with Δ attenuance as the observed feature was applied to a sample of fibrinogen deficient plasma, i.e. the fibrinogen level in such a sample is closed to zero. In this example the sample was found to have a residual fibrinogen antigen concentration of 0.0 5 g/L (detected with ELISA). Next, clotting in the fibrinogen deficient plasma was initiated with multiple thrombin concentrations (0.02, 0.06 and 1 NIH U/mL) in combination with multiple fibrinogen additions (1, 2, 3 and 4 g/L). The turbidity or attenuance for every combination was measured in four replicates for each of the (12) experimental combinations. The attenuance curves were averaged and the Δ attenuance was calculated for each experimental condition, see FIG. 3.

Next step was to fit a linear function to each of the thrombin concentrations as discussed previously (see FIG. 2). Next, the fibrinogen concentration of the original sample was inferred by using the before mentioned equation. This resulted in a fibrinogen level of 0.12 (95%-confidence interval; CI: —0.013-0.24), 0.16 (95%—CI: 0.006-0.29) and 0.033 (95%—CI: —0.074-0.13) g/L for the 0.02, 0.06 and 1 NIH U/mL of thrombin, respectively, which corresponds well with the expected fibrinogen concentration. The best results, i.e. closest to the actual fibrinogen level as determined by ELISA as well as smallest confidence interval, were obtained with 1 NIH U/mL of thrombin which is likely due to minimal impact of the feedback in the coagulation system on the clotting process.

Figure 4:
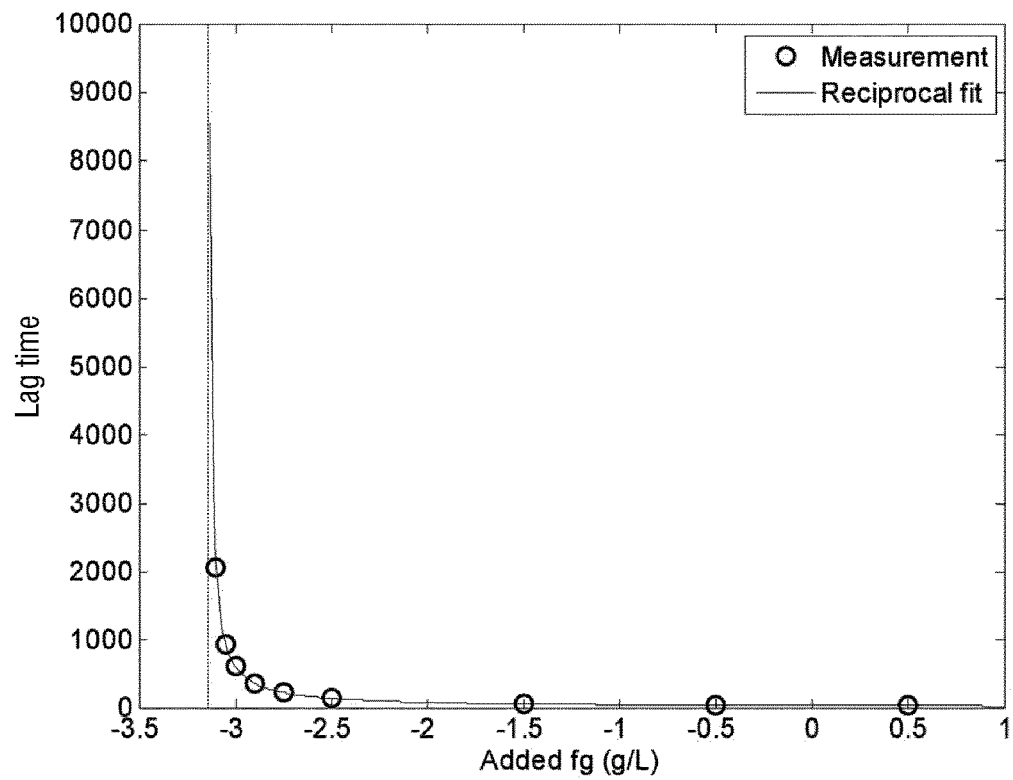
FIG. 4 shows the observed changes of lag time in seconds of the attenuance curve using a simulated fibrinogen addition experiment ranging from −3.1 (corresponding to fibrinogen extraction) to 0.5 g/L of a sample containing 3.14159 g/L fibrinogen. A reciprocal fit of the form lag time ($fg_{add}$)=85.7234/($fg_{add}$−3.1416) was found to fit the observations closely. The vertical asymptote is found at −3.1416, hence the determined concentration of fibrinogen in the sample is 3.1416 g/L which is in good agreement with the actual fibrinogen level.

Alternatively a similar approach can be followed for other extracted features of the attenuance curve that possibly demonstrate non-linear behavior for multiple fibrinogen additions. For example, features that correspond with time, e.g. lag time to (95% of) maximum attenuance, time to maximum rate (i.e. the time at which the maximum of the time derivative of the curve occur), can be fitted with e.g. an exponential, power or reciprocal function with added fibrinogen as the variable. Such features go to infinity as the true concentration of fibrinogen in the sample goes to zero as can be seen in a simulated experiment with the computer model, see FIG. 4. The horizontal (x-) coordinate of the (vertical) asymptote of the fitted curve relates to the negative value of the fibrinogen level in the sample. In case a reciprocal function of the form $\alpha/(fg_{add})-\beta)$ is fitted, which is preferred in case of the features related to points in time, with $fg_{add}$ the level of added fibrinogen and $\alpha$, $\beta$ unknown parameters that are fitted with an algorithm, $-\beta$ equals the fibrinogen level of the sample as the vertical asymptote is found at $\beta$. Another feature, the maximum rate of the attenuance curve is preferably fitted with a function of the form $\alpha*(fg_{add}-\beta)^2$, with $fg_{add}$ the level of added fibrinogen and $\alpha$, $\beta$ unknown parameters that are fitted with an algorithm. In that case the minimum of the quadratic function can be found at $\beta$, hence $-\beta$ equals the fibrinogen level of the sample as well.

Alternatively, features extracted from the average mass/length curve can be used to infer the fibrinogen concentration. For example, the maximum rates observed in the samples with added fibrinogen indicate a linear relationship between added fibrinogen and maximum rate (i.e. the maximum of the time derivative of the curve). This relation can similarly be used to infer the fibrinogen concentration of the sample. Features extracted from the average mass/length ratio pertaining to the dynamics of the curve, i.e. lag time, time to maximum rate (i.e. the maximum of the time derivative of the curve), time to (95% of) the maximally achieved mass/length ratio, can be approximated best by a reciprocal function or alternatively by a power or exponential function. The fibrinogen level of the sample can then be inferred by finding the (vertical) asymptote, as discussed previously.

Figure 5:
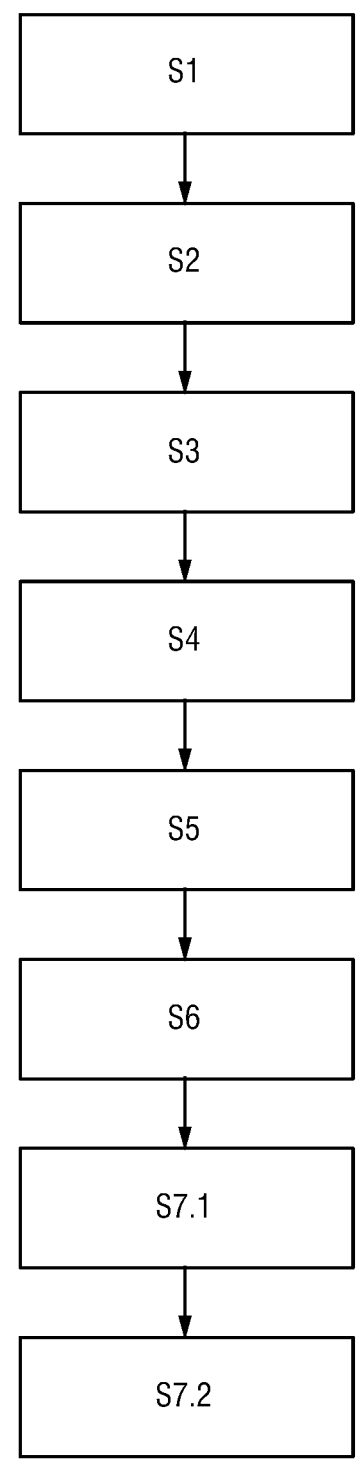
FIG. 5 schematically shows a respective flow diagram of an exemplary embodiment of the method according to the invention.

FIG. 5 schematically shows a respective flow diagram of an embodiment of the method according to the invention. In step (S1) a biological sample, such as a blood plasma sample of an individual suspected of having an altered fibrinogen concentration, is provided. In step (S2) the clotting process is started in said biological sample e.g. by the addition of a clotting trigger, such as thrombin (F2a) or snake venom thrombin-like-enzymes, respectively. In step (S3) fibrinogen is added in at least one predetermined concentration to said biological sample. It is preferred that multiple amounts of fibrinogen are added to aliquots of the sample in parallel experiments, for example divided over a cartridge with multiple detection chambers. In step (S4) the attenuance(s) of the biological sample(s) containing the added fibrinogen concentration(s) is/are determined as a function of time and a/several attenuance curve(s) is/are obtained.

In step (S5) feature values indicative of the fibrinogen concentration in said biological sample, such as the Δ attenuance, are extracted from said attenuance curve(s) and recorded as a function of fibrinogen that was added in step (S3). In step (S6) a fitted function is calculated through said recorded feature values of step (S5). In step (S7.1) said fitted function of step (S6) is extrapolated to the value of added fibrinogen where said feature value is zero or alternatively in case of features related to timing of the clotting process the value of the vertical asymptote or alternatively in case of maximum rate of the attenuance curve the value in which the quadratic fitting function has its minimum value, to obtain an extrapolated value. In step (7.2) the initial fibrinogen concentration in said biological sample is determined by multiplying said extrapolated value by −1.

While the invention has been illustrated and described in detail in the drawings and foregoing description, such illustration and description are to be considered illustrative or exemplarily and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the undefined article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A method for determining an initial fibrinogen concentration in a biological sample using an optical measuring system, the method comprising:
   providing a biological sample to a container of the optical measuring system;
   adding fibrinogen to a first portion of said biological sample at a first predetermined fibrinogen concentration, wherein a second portion of said biological sample is without any added fibrinogen;
   adding a clotting trigger to said first portion and second portion of said biological sample to start a clotting process, wherein said clotting trigger is added in a concentration sufficiently high that a shape of an attenuance curve is determined by the fibrinogen concentration in the first portion and second portion of said biological sample;

determining attenuance of the biological sample as a function of time to obtain an attenuance curve, comprising: (i) exposing the first portion and second portion of said biological sample in the container to light from a light source of the optical measuring system, and (ii) measuring the light using a light detector of the optical measuring system;

receiving, by a calculating unit of the optical measuring system, the light measurement from the light detector; and determining, by the calculating unit, the initial fibrinogen concentration in the biological sample, comprising: (i) extracting feature values indicative of the fibrinogen concentration in said biological sample from said attenuance curve; (ii) recording the feature values as a function of the added fibrinogen; (iii) calculating a fitted function through said recorded feature values; and (iv) determining the initial fibrinogen concentration in said biological sample from said fitted function.

2. The method of claim 1, wherein the feature values indicative of the fibrinogen concentration in said biological sample are selected from the group consisting of:
a difference in attenuance of said biological sample between a first point in time and a second point in time ($\Delta$ attenuance);
a maximum attenuance rate (time derivative of attenuance curve); and
features which correspond with time.

3. The method of claim 2, wherein the difference in attenuance of said biological sample is measured between a first point in time and a second point in time, wherein a starting point of the clotting process is the first point in time, and an end of the clotting process is the second point in time.

4. The method of claim 1, wherein said fitted function is selected from the group consisting of a linear function, a non-linear function, an exponential function, a power function, and a reciprocal function.

5. The method of claim 1, wherein said container is a multi-well container configured to receive at least two aliquots of said biological sample.

6. The method of claim 1, wherein the clotting trigger is selected from the group consisting of active coagulation factors; snake venom thrombin-like enzymes; kaolinite, micronized silica, and ellagic acid.

7. The method of claim 6, wherein the clotting trigger is an active coagulation factor selected from the group consisting of thrombin (F2a), tissue factor (TF), active FX (FXa), active proconvertin (FVIIa), and a mixture thereof.

8. The method of claim 6, wherein the clotting trigger is a snake venom thrombin-like enzyme selected from the group consisting of batroxobin, reptilase, and a mixture thereof.

9. The method of claim of claim 1, further comprising:
wherein the step of adding fibrinogen further comprises adding fibrinogen to a third portion of said biological sample at a second predetermined fibrinogen concentration; and
wherein determining attenuance of the biological sample comprises: (i) exposing the third portion of said biological sample in the container to light from the light source of the optical measuring system, and (ii) measuring the light using the light detector of the optical measuring system.

* * * * *